(12) United States Patent
Young et al.

(10) Patent No.: US 8,277,831 B2
(45) Date of Patent: Oct. 2, 2012

(54) DRUG-ENHANCED ADHESION PREVENTION

(75) Inventors: Janel E. Young, New Hope, PA (US); Scott A. Wadsworth, New Hope, PA (US); Kevin Cooper, Flemington, NJ (US); Joel Rosenblatt, Watchung, NJ (US); Han Cui, Bridgewater, NJ (US)

(73) Assignee: Advanced Technologies and Regenerative Medicine, LLC., Raynham, MA (US)

( * ) Notice: Subject to any disclaimer, the term of this patent is extended or adjusted under 35 U.S.C. 154(b) by 2306 days.

(21) Appl. No.: 10/780,452

(22) Filed: Feb. 17, 2004

(65) Prior Publication Data

US 2005/0181023 A1    Aug. 18, 2005

(51) Int. Cl.
    *A61F 2/02* (2006.01)
(52) U.S. Cl. ........................................ 424/423
(58) Field of Classification Search .................. None
    See application file for complete search history.

(56) References Cited

U.S. PATENT DOCUMENTS

| | | | |
|---|---|---|---|
| 5,034,230 A * | 7/1991 | Morita et al. ............... | 424/427 |
| 5,532,221 A | 7/1996 | Huang et al. | |
| 5,665,428 A | 9/1997 | Cha et al. | |
| 5,711,958 A | 1/1998 | Cohn et al. | |
| 5,760,200 A | 6/1998 | Miller et al. | |
| 5,783,691 A | 7/1998 | Malson et al. | |
| 6,124,273 A | 9/2000 | Drohan et al. | |
| 6,127,348 A | 10/2000 | Roufa et al. | |
| 6,133,325 A | 10/2000 | Schwartz et al. | |
| 6,166,130 A | 12/2000 | Rhee et al. | |
| 6,214,384 B1 | 4/2001 | Pallado et al. | |
| 6,280,745 B1 | 8/2001 | Flore et al. | |
| 6,306,424 B1 | 10/2001 | Vyakamam et al. | |
| 6,333,029 B1 | 12/2001 | Vyakamam et al. | |
| 6,355,699 B1 | 3/2002 | Vyakamam et al. | |
| 7,056,591 B1 * | 6/2006 | Pacetti et al. ............... | 428/480 |
| 2002/0001609 A1 | 1/2002 | Calhoun et al. | |
| 2002/0055701 A1 | 5/2002 | Fischell et al. | |
| 2004/0225077 A1 | 11/2004 | Gravett et al. | |

OTHER PUBLICATIONS

Pemirolast, PDR, pp. 1-7, 2007.*
Pemirolast, Rxlist.com, p. 5, 2007.*
Pemirolast, Advanced Consumer Information, pp. 1-3, 2007.*
Casey K. Lee et al., Spine 9(3) 305 (1984).
T. Kitano et al., Spine 16(7) 820 (1991).
Jerome R. Wujek el al., Experimental Neurology 114 237 (1991).
Stephen D. Cooki et al., Spine 19(16) 1815 (1994).
Y. He et al., Spine 20(5) 557 (1995).
Jeffrey S. Ross et al., Neurosurgery 38(4) 855 (1996).
Douglas B. Johns et al., Fertility and Sterility 68(1) 37 (1997).
Naoki Okuyama et al., J. Surgical Research 78 118 (1998).
R. John Kurlbert et al., J. Neurosurger(Spine 2) 90 191 (1999).
H. Osada et al., J. International Medical Research 27 292 (1999).
Fred H. Geisler. Neurological Research 21 Supplement 1, S9 (1999).
Peter B. Arnold et el., Fertility and Sterility 73(1) 157 (2000).
Kathleen E. Rodgers et al., Fertility and Sterility 73(4) 831 (2000).
Ali M. Ghellai et al., J. Gastrointest Surg 4 310 (2000).
Song Liu et al., J. Neurosurger(Spine 1) 94 61(2001).
Peter Lundorff et al., Human Reproduction 16(9) 1982 (2001).
Lin-Shu Liu el al., J. Biomed Mater Res (Appl Biomater) 63 326 (2002).
Kathleen E. Rodgers et al., The Spine Journal 3 277 (2003).
PCT International Search Report PCT/US05/05089 dated May 16, 2005.
Kathleen E. Rodgers, Ph.D., "Nonsteroidal Anti-Inflammatory Drugs (NSAIDs) in the Treatment of Postsurgical Adhesion", Treatment of Post Surgical Adhesions, 1990, pp. 119-129.
Gere S. Dizerega et al., "Prevention of Postoperative Adhesions", The Peritoneum, Springer-Verlag, New York, pp. 307-369 (1992).

* cited by examiner

*Primary Examiner* — Carlos Azpuru
(74) *Attorney, Agent, or Firm* — Roberts Mlotkowski Safran & Cole, P.C.

(57) ABSTRACT

The present invention includes methods for the inhibition of post-operative adhesion formation between tissue surfaces in a body cavity having been subjected to a surgical procedure, which methods involve administering Pemirolast, or an analog thereof, directly to tissue surfaces in the body cavity in amounts and under conditions effective to inhibit formation of adhesions, and to delivery vehicles and compositions suitable for use for local, non-systemic administration of a drug to the body and directly to tissue within a body cavity having been subjected to a surgical procedure.

16 Claims, No Drawings

DRUG-ENHANCED ADHESION PREVENTION

FIELD OF THE INVENTION

The present invention relates to the use of Pemirolast, or analogs thereof, to inhibit or prevent post-operative adhesion formation between tissue surfaces in a body cavity and to compositions or drug delivery devices containing Pemirolast or an analog thereof for local, non-systemic administration thereof to the body for inhibition or prevention of post-operative adhesions.

BACKGROUND OF THE INVENTION

Adhesion formation, in particular following peritoneal, thoracic, and spinal surgery, for example, is a major source of postoperative morbidity and mortality. Appendectomy and gynecologic surgery, for example, are the most frequent surgical procedures implicated in clinically significant adhesion formation. The most serious complication of intraperitoneal adhesions is intestinal obstruction. In addition, adhesions are associated with chronic or recurrent pelvic pain and infertility in females, nerve compression and pain in the spine, post-operative complications following thoracic surgery, and loss of mobility in the hand after reconstructive surgery.

The pathogenesis of adhesion formation is complex and not entirely understood. The first step is believed to involve excess fibrin deposition to form a scaffold. Organization of the fibrin scaffold by cellular elements, including cells such as fibroblasts, then follows.

Various approaches for the prevention of adhesion formation have been actively explored (dizerega, G. S. & Rodgers, K. E., "Prevention of Postoperative Adhesions," in "The Peritoneum," dizerega, G. S. & Rodgers, K. E., eds., Springer-Verlag, New York, pp. 307-369 (1992)). In general, the treatments fall into one of several categories: limiting tissue apposition; reduction of local tissue inflammation; prevention of fibrin deposition and removal of fibrin deposits; reduction of the proliferation of cells such as fibroblasts; and collagen inhibition.

For example, physical barriers have been used in attempts to prevent adhesion formation by limiting tissue apposition during the critical period of healing, thereby minimizing the development of fibrin matrix between tissue surfaces. Barrier agents that have been employed include both mechanical barriers and viscous solutions. Mixed efficacy results have been obtained using film barriers such as poly(tetrafluoroethylene). Such a membrane also is less than ideal, as it must be sutured into place and is nonabsorbable. Absorbable barriers would be preferable, but some studies have demonstrated the efficacy of such barriers to be less than ideal in preventing adhesions. Liquid barriers also have been considered for use in preventing adhesions; for example, both chondroitin sulfate and carboxymethyl cellulose have shown some promise in animal models.

Anti-inflammatory drugs have been evaluated for their effects on postoperative adhesion formation, as they may limit the release of fibrinous exudate in response to inflammation at the surgical site. Two general classes of these drugs have been tested: corticosteroids and nonsteroidal anti-inflammatory drugs. The results of corticosteroid use in animal studies generally have not been encouraging, and clinical use of corticosteroids is limited by their other pharmacological properties. Nonsteroidal anti-inflammatory drugs show promise for inhibition of postoperative adhesion formation (Rodgers, K. E., "Nonsteroidal anti-inflammatory drugs (NSAIDs) in the treatment of Postsurgical adhesion," in "Treatment of Post-Surgical Adhesions," dizerega, G. S. et al., eds., Wiley-Liss, New York, pp. 119-129 (1990)).

Another approach that has been explored involves the removal of fibrin deposits. Although proteolytic enzymes (e.g., pepsin, trypsin and papain) should theoretically augment the local fibrinolytic system and limit adhesion formation, these enzymes are neutralized rapidly by peritoneal exudates, rendering them virtually useless for adhesion prophylaxis. While various fibrinolytics, for example, fibrinolysin, streptokinase and urokinase, have been advocated, a potential complication to the clinical use of these enzymes in postoperative therapy is excessive bleeding resulting from their administration.

Lastly, collagen inhibitors have been evaluated. The biosynthesis of collagen involves unique post-translational modification of pro-alpha chains. Hydroxylation of prolyl and lysyl residues, a key step in collagen formation, is vital for normal triple-helix formation and intermolecular cross-linking. When post-translational processing is inhibited, non-helical procollagen forms, which then is degraded by intracellular proteases and secreted into the extracellular matrix at a slow rate as a nonfunctional protein. The incorporation of proline analogs, e.g., cis-4-hydroxy-L-proline (cHyp) into nascent pro-alpha chains has been shown to reduce the extracellular accumulation of collagen. Such agents are believed to act more generally by inhibiting collagen synthesis and thereby averting certain of the pathophysiological sequelae of fibrosis, such as atherosclerosis and hypertension. Through the distortion of bond angles and from steric hindrance among polypeptide chains, cHyp inhibits the folding of pro-alpha chains into a stable triple helix. Other proline analogs, such as cis-4-fluoroproline, cis-4-bromoproline, and 3,4-dehydroproline, have similar effects, but also can inhibit other post-translational steps. The compound 3,4-dehydroproline is an example of a proline analog that also can inhibit other post-translational steps. For example, 3,4-dehydroproline inhibits prolyl hydroxylase activity. Unfortunately, it also is recognized that cHyp can inhibit wound healing if used improperly, particularly in chronic use, and thus has had limited clinical utility.

The compound 9-methyl-3-(1H-tetrazol-5-yl)-4H-pyrido[1,2-α]pyrimidin-4-one potassium, commonly known as Pemirolast, has not been examined as an adhesion prevention agent.

Therefore, it would be advantageous to provide improved treatments to inhibit or prevent the formation of post-operative adhesions, as well as compositions or delivery devices for use in such treatments utilizing Pemirolast. The present invention provides such improvements in the surprising discovery that Pemirolast may be delivered directly to the surgical site, either alone or by drug delivery compositions or devices, to inhibit or prevent the formation of such adhesions.

SUMMARY OF THE INVENTION

The present invention is directed to methods for the inhibition of post-operative adhesion formation in a body between tissue surfaces in a body cavity having been subjected to a surgical procedure comprising administering Pemirolast, or an analog thereof, directly to tissue surfaces in the body cavity in amounts and under conditions effective to inhibit formation of adhesions thereon, and to delivery vehicles and compositions suitable for use for non-systemic administration of a drug directly to tissue within a body cavity having been subjected to a surgical procedure, where the vehicle or composition comprises Pemirolast in an amount effective to inhibit formation of post-operative adhesions upon administration of the Pemirolast to the tissue under conditions effective to provide inhibition of post-operative adhesions in the body cavity.

DETAILED DESCRIPTION OF THE INVENTION

Compositions according to the present invention, methods for their administration and delivery vehicles suitable for use in non-systemic administration of such compositions to the body tissue are useful in inhibiting or preventing formation of adhesions between tissue and/or organ surfaces, the most common cause of which is prior surgery. While prevention of the formation of any adhesions after surgery would be preferred, it is sufficient to inhibit formation of such adhesions such that the degree or extent of adhesion formation is low enough not to present serious problems associated with adhesion formation, such as are described herein.

The inventive methods and compositions have been shown to be especially effective in inhibiting adhesion formation in the peritoneum following surgery. In addition, the present invention finds utility in other contexts, e.g., for cardiovascular, orthopedic, thoracic, ophthalmic, CNS, reconstructive surgery, e.g. hand, and other uses, where the formation of adhesions is a significant concern. In addition, inhibition of adhesion formation or drug loculation during the intraperitoneal administration of a chemotherapeutic agent, or inhibition of adhesion formation or drug loculation during the administration of a pain medication such as morphine also would be desirable. As such, the combination of Pemirolast with compositions containing the chemotherapeutic agent or other therapeutic agents in order to provide not only the therapeutic affect sought by the therapeutic agents, but also to inhibit the formation of adhesions that may form as a result of administration of such compositions, are encompassed by the scope of the present invention.

The present invention is based on the discovery that Pemirolast, also know as 9-methyl-3-(1H-tetrazol-5-yl)-4H-pyrido[1,2-α]pyrimidin-4-one potassium, or analogs thereof, a compound know for treating inflammation, allergies and asthma, is useful in reducing or preventing formation of adhesions between tissue surfaces in body cavities following surgical procedures when administered directly to the tissue and body cavity in amounts and under conditions effective to inhibit the formation of post-operative adhesions.

The processes that are involved in adhesion formation include, but are not limited to inflammatory responses, cell growth and differentiation, angiogenesis, extracellular matrix turnover, tissue remodeling, and apoptosis (Chegini, N (2002), "Peritoneal Molecular Environment, Adhesion Formation and Clinical Implication," Frontiers in Bioscience 7, e91-115, Apr. 1, 2002).

Though specific embodiments disclosed herein exemplify Pemirolast as a useful compound for inhibiting or preventing post-surgical adhesion formation, it is understood that analogs and derivatives of Pemirolast also are contemplated as being suitable for use in the present invention. Suitable analogs and derivatives of Pemirolast include, 3-(1H-Tetrazol-5-yl)-4H-pyridol[1,2-α]pyrimidin-4-one, 7-Methyl-3-(1H-Tetrazol-5-yl)-4H-pyridol[1,2-α]pyrimidin-4-one, 8-Methyl-3-(1H-Tetrazol-5-yl)-4H-pyridol[1,2-α]pyrimidin-4-one, 7-Ethyl-3-(1H-Tetrazol-5-yl)-4H-pyridol[1,2-α]pyrimidin-4-one, 7-n-Butyl-3-(1H-Tetrazol-5-yl)-4H-pyridol[1,2-α]pyrimidin-4-one, 7-Phenyl-3-(1H-Tetrazol-5-yl)-4H-pyridol[1,2-α]pyrimidin-4-one, 7-Chloro-3-(1H-Tetrazol-5-yl)-4H-pyridol[1,2-α]pyrimidin-4-one, 7,9-dimethyl-3-(1H-Tetrazol-5-yl)-4H-pyridol[1,2-α]pyrimidin-4-one, 9-Ethyl-3-(1H-Tetrazol-5-yl)-4H-pyridol[1,2-α]pyrimidin-4-one, 8,9,1-,11-tetrahydro-3-(1H-Tetrazol-5-yl)-4H-pyrimido[2,1-α]isoquinol-4-one. It is also understood that Pemirolast analoguees can include non-potassium salts of Pemirolast such as sodium, calcium, and magnesium salts, and the free acid 9-methyl-3-(1H-tetrazol-5-yl)-4H-pyrido[1,2-α]pyrimidin-4-one potassium.

Preferred Pemirolast analogs and derivatives are those that exhibit little or no toxicity both at the local and systemic level and are suitable for use in animals, including humans. One skilled in the art will be able to readily identify those analogs once having the benefit of this disclosure.

Pursuant to the present invention, Pemirolastor analogs thereof are administered and maintained at an effective concentration at the site of potential adhesion formation for a period of time sufficient to prevent adhesion formation. Pemirolastor analogs thereof typically are administered to the body cavity over a post-operative interval until healing of the wound site is complete. In some embodiments, Pemirolast may be delivered in a single dose and maintained in contact with the tissue in the body cavity as described herein. In other embodiments, Pemirolast may be delivered in a series of doses timed to continue the administration over a period of time sufficient to inhibit adhesion formation, i.e. by sustained release.

The therapeutically effective concentrations of Pemirolast or analogs thereof are ones that inhibit or prevent post-surgical adhesion formation between tissue surfaces in body cavities having undergone surgery when applied to tissue in the body cavity. The minimum amount of Pemirolast or analogs thereof that can be administered must be effective to inhibit formation of the postoperative adhesion, as described herein. The maximum amount of Pemirolast or analog thereof that may be administered is limited by the toxicity of the compound. In general, the range of concentration of Pemirolast administered to the body will be from about 0.01 milligram Pemirolast per kilogram of the body to about 3,000 milligram Pemirolast per kilogram of the body.

According to methods of the present invention, Pemirolast is administered directly to a targeted injury site following the surgical procedure conducted at the site in cooperation with a delivery vehicle suitable for non-systemic administration of a drug to tissue of the body, for example, a poly(ethylene glycol)/sodium carboxymethylcellulose aqueous gel, in order to reduce, or inhibit, or prevent adhesion formation at the site after surgery. Preferably, Pemirolast is administered in a single dose prior to skin closure after surgery using a delivery vehicle that enables the maintenance of requisite effective concentrations of the compound for a period of time sufficient to prevent adhesion formation during healing of the site. A suitable delivery vehicle itself essentially would be non-inflammatory and non-immunogenic and would permit release of Pemirolast so as to maintain effective levels thereof over the desired period of time.

A large variety of alternative sustained release delivery vehicles for administering Pemirolast or analogs thereof also are contemplated as within the scope of the present invention when containing therapeutically effective amounts of Pemirolast. Suitable delivery vehicles include, but are not limited to, microcapsules or microspheres; liposomes and other lipid-based release systems; absorbable and/or biodegradable mechanical barriers; emulsions, the emulsion either being a liquid polymer plus surfactant or a non-aqueous polymer solution plus surfactant in an aqueous carrier; polymeric delivery materials such as, but not limited to, polyethylene oxide/polypropylene oxide block copolymers (i.e., poloxamers), poly(orthoester)s, poly(vinyl alcohol)s, poly(anhydride)

s, poly(methacrylate)s, poly(methacryladmide)s, anionic carbohydrate polymers, poly(hydroxybutyric acid)s, and polyacetals. Most preferably, a suitable formulation to achieve the most desired release profile of Pemirolast, near pseudo zero-order, comprises injectable microcapsules or microspheres prepared from a biodegradable polymer such as, but not limited to, poly(l-lactide), poly(dl-lactide), poly (dl-lactide-coglycolide)s, poly(l-lactide-co-glycolide)s, poly (ecaprolactone), polyglycolide, poly(p-dioxanone)s, poly(trimethylene carbonate), poly(alkylene diglycolate)s, poly (oxaester)s, poly(oxaamide)s, glycerides, and copolymers and blends thereof. Other desired release profiles, such as ones that yield an initial burst release of Pemirolast followed by zero-order sustained release, may be created by mixing encapsulated and non-encapsulated drug into the formulation.

Glycerides, long chain carboxylic acid esters, that may be used according to the present invention, include, but are not limited to glyceryl monostearates; glyceryl monopalmitates; mixtures of glyceryl monostearate and glyceryl monopalmitate (Myvaplex 600, available from Eastman Fine Chemical Company, Rochester, N.Y.); glyceryl monolinoleate; glyceryl monooleate; mixtures of glyceryl monopalmitate, glyceryl monostearate, monooleate and glyceryl monolinoleate (Myverol Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Myverol 18-99, Eastman Fine Chemical Company); acetylated glycerides such as distilled acetylated monoglyceride (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); d-alpha tocopherol polyethylene glycol 1000 succinate (Vitamin E TPGS, Eastman Fine Chemical Company); mixtures of mono- and di-glyceride esters; calcium stearoyl lactylate; ethoxylated mono- and di-glycerides; lactated mono- and di-glycerides; lactylate carboxylic acid esters of glycerol and propylene glycol; lactylic esters of long chain carboxylic acids; polyglycerol esters of long chain carboxylic acids; propylene glycol mono- and di-esters of long chain carboxylic acids; sodium stearoyl lactylate; sorbitan monostearate; sorbitan monooleate; other sorbitan esters of long chain carboxylic acids; succinylated monoglycerides, stearyl monoglyceryl citrate; stearyl heptanoate; cetyl esters of waxes; stearyl octanoate; C10 to C30 cholesteroulavosterol esters; and sucrose long chain carboxylic acid esters.

These glycerides may be used singly or in combination with other glycerides such as, but not limited to, triglyceryl esters such as glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate glyceryl monocaprate, glyceryl dicaprate, glyceryl tricaprate, glyceral monomyristate, glyceryl dimyristate, glyceryl trimyristate, glyceryl monodecenoate, glyceryl didecenoate and glyceryl tridecenoate.

Injectable systems comprising microcapsules or microspheres of a diameter on the order of about 1 to about 1,000 microns offer advantages over other delivery systems since such systems inherently are flexible in the design of the duration and rate of separate drug release by selection of microcapsule size, drug loading and dosage administered. In addition, such microcapsules can be sterilized successfully by means such as gamma irradiation or ethylene oxide.

Microspheres and microcapsules are vehicles or systems comprising a polymeric wall that encloses a liquid or solid core. The microshpere wall usually does not react with the core material; however, it is designed to provide sufficient strength to enable normal handling without rupture while being sufficiently thin to allow a high core to wall volume ratio. The sphere/capsule contents remain within the wall until released by diffusion or other means that dissolve, melt, break, rupture or remove the material contained within the sphere/capsule. Preferably, the sphere/capsule wall can be made to degrade and decompose in suitable environments, thus allowing diffusion of the core material through the capsule wall to provide for its slow, sustained delivery.

The mechanism of release in biodegradable microspheres is a combination of drug diffusion and polymer biodegradation. Therefore, the rate and duration of release are determined by microsphere size, drug content and quality, and polymer parameters such as crystallinity, molecular weight and composition. In particular, adjustment in the amount of drug released is generally achieved by modification of wall thickness, diameter, or both.

Moreover, alternative delivery systems based on biodegradable polymers and that are suitable for use in accordance with the present invention, for example, fibers, films, foams, or filaments comprising the active agents, also are contemplated as being within the scope of the present invention when containing effective amounts of Pemirolast or analogs thereof.

An alternate approach for the single-dose-delivery of Pemirolast involves the use of biodegradable polymers, such as the ones described above, in the form of a film. Such films may be produced by spraying or discharging dispersed liquid droplets containing the biopolymer and Pemirolast in a suitable carrier from a pressurized container onto the targeted site.

Such films, fibers, foams, and particles can be prepared by a variety of processes known to those skilled in the art. Such processes include, but are not limited to, spinning disc, solution/precipitation processes, compression molding, injection molding, extrusion, and supercritical fluid processes.

Another approach for the single-dose delivery of Pemirolast, in accordance with the present invention, involves the use of liposomes and other lipid-based delivery systems to encapsulate the active agent in multilamellar vesicles (or liposomes). In a typical procedure, a liposome-forming powdered lipid mixture is added to the desired quantity of active agent in aqueous solution, e.g. phosphate buffered saline, to form a suspension. After a suitable hydration period, the hydrated suspension then is autoclaved to provide the liposome-active agent preparations.

The composition of the liposome may comprise a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and egg phosphatidylcholine.

A lipid mixture suitable for formation of liposomes may be prepared from L-alpha-distearoyl phosphatidylcholine and cholesterol dissolved in chloroform, to which alpha-tocopherol is added. Other compositions and methods for formation of liposomes also would be useful for this purpose and will be apparent to those skilled on the art once having the benefit of the present disclosure.

Hyaluronan modified liposomes and PEG modified liposomes also are contemplated as delivery vehicles for use in this invention.

Other lipid-based delivery systems also are contemplated for use in this invention. One useful system includes lipid foams such as those available under the tradename DEPOFOAM (SkyPharama, Inc., San Diego, Calif.), which are extended-release formulations comprising spherical particles bounded by a single bilayer lipid membrane, each containing numerous nonconcentric aqueous chambers which encapsulate the active ingredient. Such lipid particles are made from nontoxic lipids identical to those found in cell membranes.

Another suitable approach for single dose delivery of Pemirolast in accordance with the present invention involves the use of crystalloid and so-called viscous instillates. Crystalloids are known in the art as water-soluble crystalline substances, e.g. NaCl, capable of diffusing through a semi-permeable membrane. Solutions of crystalloids, such as saline, are known as crystalloids, crystalloid solutions or crystalloid instillates. Crystalloid instillates include, but are not limited to, lactated Ringer's solution, saline and phosphate buffered saline. In the case of viscous instillates, high-molecular-weight carriers used in admixture with the active agents include, but are not limited to, dextrans and cyclodextrans; hydrogels; cross-linked viscous materials, including viscoelastics and cross-linked viscoelastics; carboxymethylcellulose; poly(saccharide)s; hyaluronic acid; cross-linked hyaluronic acid and hyaluronic acid compounded with orthoesters.

Crosslinked hyaluronic acid-based adhesion prevention barriers include; 1,4 butanediol diglycidyl ether crosslinked hyaluronic acid, available under the tradenames RESTYLANE and PERLANE Q-Med Aktiebolag Corporation, Uppsala Sweden); aldehyde crosslinked hyaluronans, available under the tradename SYNVISC (Biomatrix, Inc., Ridgefield, N.J.); biscarbodiimide crosslinked hyaluronans, available under the tradename INCERT (Anika Therapeutics, Inc., Woburn, Mass.); internally esterified hyaluronan, available under the tradename ACP (Fidia Farmaceutici SpA, Terme, Italy); hyaluronans cross-linked using vinyl sulfone, bisepoxide, hydrazide; photo-crosslinked hyaluronans; and Carbodiimide modified Hyaluronan and CMC, available under the tradenames SEPRAFILM and SEPRAGEL (Genzyme Corporation, Framingham Mass.).

In another preferred embodiment of the present invention, a delivery vehicle in the form of a barrier and Pemirolast could show greater efficacy if combined with other drugs at the time of surgery or pre-operatively. For example, an anti-fibrotic such as the recombinant plasminogen activator compound available under the tradename RETAVASE (Boehringer Mannheim Corp., Indianapolis, Ind.) would be delivered to the site at the time of surgery and then a barrier/collagen synthesis inhibitor (such as Pemirolast) would be placed onto the site. The combined effect of the plaminogen activator compound limiting the clotting at the surgical site, the barrier limiting the apposition of the tissue surfaces and the Pemirolast inhibiting collagen synthesis could dramatically reduce adhesions. The additional therapeutic agents also could be given systemically, by a variety of means, prior to, during or after surgery in conjunction with local, non-systemic administration post-operatively. In addition, Pemirolast may be administered systemically in conjunction with local, non-systemic administration of Pemirolast.

Therapeutic agents that may be used in combination with Pemirolast may fall in the general classes of anti-platelet, anti-fibrotic, anti-inflammatory, anti-proliferative, and/or inhibit collagen synthesis. These include, but are not limited to, Urokinase, the nonglycosylated deletion mutein of tissue plasminogen activator available under the tradename RETAVASE (Boehringer Manheim, Indianapolis, Ind.), pharmaceutical preparations containing abciximab for the prevention and treatment of diseases of the circulatory system available under the tradename REOPRO (Eli Lilly and Company, Indianapolis Ind.), Clopidogrel Bisulfate, available under the tradename PLAVIX (Sanofi-Synthelabo, Paris, France), pharmaceutical preparations containing imatinib mesylate for use in the field of oncology available under the tradename GLEEVEC (Novartis AG, Basel Switzerland), Triamcinolone Acetonide, Tepoxalin, Pirfenidone, collagenase, anti-CTGF, tyrosine kinase inhibitors, prolyl hydroxylase inhibitors, lysly oxidase inhibitors, C-proteinase inhibitors, N-proteinase inhibitors, TGF-beta inhibitors such as Tamoxifen, HMG-CoA Reductase inhibitors such as Lovastatin, COX-1 and/or COX-2 inhibitors such as Ibuprofen, Nimesulide, pharmaceutical preparation containing vofecoxib for the treatment of arthritis available under the tradename VIOXX (Merck & Co., Inc. Whitehouse Station N.J.), pharmaceuticals in the nature of anti-inflammatory analgesics containing celecoxib available under the tradename CELEBREX (G.D. Searle & Co., Skokie Ill.), pharmaceutical preparations containing valdecoxib available under the tradename BEXTRA (Pharmacia & Upjohn Co., North Peapackn N.J.), Calcium ion inhibitors such as Amlodipine, Nifedipine, pharmaceuticals such as verapamil used in the treatment of hypertension, iron chelators such as deferoxamine available under the tradename DESFERAL (Novartis AG, Basel Switzerland), antibiotics such as Clarithromycin and Ciprofloxin retinoids such as Tretinoin and Retinoic Acid, chymase inhibitors, mast cell stabilizers such as Cromolyn, available under the tradenames OPTICROM or CROLOM (Bausch Lomb Pharmaceuticals, Inc. Tampa, Fla.), Lodoxamide, available under the tradename ALOMIDE (Alcon Laboratories, Inc. Fort Worth, Tex.), Nedocromil (ALOCRIL Allergan, Inc. Irvine, Calif.), Pimecrolimus, available under the tradename ELIDEL (Novartis AG Corporation Basel, Switzerland), Amlexanox, Epinastine, dual action mast cell stabilizers and H1 receptor antagonists such as Olopatadine, available under the tradename PATANOL (Alcon Manufacturing, Ltd Fort Worth, Tex.), Ketotifen, available under the tradename ZADITOR (Novartis AG Corporation Basel, Switzerland), Azelastine, available under the tradename OPTIVAR (ASTA Medica, Inc., Tewksbury, Mass.), Pemirolast, and analogs thereof, and anti-thrombin drugs or thrombolytics, such as bivalirudin, available under the tradename ANGIOMAX (The Medicines Company, Cambridge Mass.). When used in combination with Pemirolast, the therapeutic agents, or drugs, are present in an amount effective to provide the therapeutic effect intended by administration of the therapeutic agent.

In one embodiment of the invention, Pemirolastis combined with a physical barrier. It is believed that for a combination of the proper physical barrier and Pemirolast, an unexpected synergistic effect could be created that yields results better than either Pemirolastor barrier used alone. For example, a barrier comprising a polyethylene glycol whose surface properties are antithrombogenic, and therefore could prevent platelet adherence, could prevent some fibrin clotting from occurring. At the same time, Pemirolastor an analog thereof that affects a later event in the adhesion sequence, e.g. collagen synthesis, could be delivered to the site over an extended period of time. Hence, by affecting more than one adhesion-producing event, the Pemirolast/barrier combination will have efficacy that is greater than the sum of the Pemirolastand barrier. Other barriers also could exhibit such effects in combination with Pemirolast.

As another example, hyaluronic acids have been proposed to reduce cell proliferation (anti-proliferative) as well as being excellent coatings that would provide a lubricious surface between apposed tissue surfaces. The body excretes hyaluronic acid for just such a purpose, i.e., articulating surfaces-joints. Such a barrier could be, for example, a polymeric carboxymethylcellulose gel that is hydrophilic, so that it adheres to the tissues of the site, and has excellent biocompatibility, so that it does not cause an inflammatory response that could elicit collagen synthesis. Combined with Pemirolast, a hyaluronic acid barrier could be more effective than Pemirolastor itself.

Other barriers include, but are not limited to, crosslinked albumin, albumin based gels, various derivatives of hyaluronic acids (salts such as iron, sodium; esters such as benzyl); cellulosics derivatives (oxidized regenerated; methyl; ethyl; hydroxypropyl); collagens; recombinant human collagen; polyethylene glycols (including in-situ crosslinked); pluronics; chitin, chitosans; dextrans; glucoses; carbohydrates; gelatins; glycosaminoglycans; polyacrylamides; polyvinyl pyrrolidones; polyvinyl alcohols; polymethyacrylics; aliginates; starches; polypeptides; and any other water soluble polymer and blends thereof. Such polymers could also be copolymerized or blended with hydrolyzable or enzymatically degradable polymers such as polylactones, polyoxaesters, polyalkylene diglycolates, and glyceride containing polymers, and copolymer and blends thereof. Barriers also could be non-absorbable barriers such as polytetrafluoroethylene. Pemirolastand/or other therapeutics of the present invention may be covalently or non-covalently (e.g., ionically) bound to such a barrier, or it may simply be dispersed therein.

It also should be known that the delivery vehicles described herein not only may include a barrier such as a gel that would deliver the drug locally, but also could include delivery of the drug(s) via other local administration methods such as an osmotic pump.

The invention may be better understood with reference to the accompanying examples, which are intended to be illustrative only and should not be viewed as in any sense limiting the scope of the invention, which is defined hereinafter in the accompanying claims.

EXAMPLES

Studies to confirm the efficacy of Pemirolastin the reduction or inhibition of adhesion formation after peritoneal surgery were performed using a sidewall adhesion model.

In the peritoneal sidewall model, rabbits were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3 cm×5 cm area of peritoneum and transversus abdominis muscle was removed on the right lateral abdominal wall. The cecum was exteriorized and digital pressure was exerted to create subserosal hemorrhages (trauma and loss of blood flow) over all cecal surfaces. The cecum was then returned to its normal anatomic position. Pemirolast contained in a delivery vehicle as described below was placed in an Alzet® miniosmotic pump (Alza Corporation, Palo Alto, Calif.) to allow continuous release of the molecule through the postsurgical interval. The Alzet miniosmotic pump was placed in the subcutaneous space and a delivery tube connected the pump with the site of injury at the sidewall. Only the delivery vehicle was placed in the pump of control rabbits. The abdominal wall and skin were closed in a standardized manner.

After 21 days, the rabbits were sacrificed and the percentage of the area of the sidewall injury that was involved in adhesions was determined. In addition, the tenacity of the adhesion formed was scored using a system as follows:

0=No adhesions; 1=mild, easily dissectible adhesions; 2=moderate adhesions; non-dissectible, does not tear organ; 3=dense adhesions; non-dissectible, tears when removed. With the sidewall model, an initial score to represent the overall extent of adhesions is given (0 to 3).

The percentage of a surface of the sidewall involved in adhesions to various organs are given in the tables below to quantify the overall adhesion score. A reduction in the area and the tenacity of the adhesions would be considered beneficial and efficacious.

Example 1

Sidewall Model Evaluation of Pemirolast: 1 Week Dosing

The efficacy of Pemirolast in inhibiting adhesion formation was evaluated using a single pump, filled with one of three dosage levels of mg of Pemirolast per ml of delivery vehicle (0.625 mg/ml, 6.25 mg/ml or 62.5 mg/ml), or placebo control (saline). The drug was placed in an Alzet miniosmotic pump and delivered over 7 days at a rate of 10 microliter/hr. The animals were sacrificed after 21 days.

Tables 1 to 4 show the adhesion area percentage and adhesion tenacity for all rabbits in all study groups. The tables show that, relative to the control, Pemirolast administration reduced the area of adhesion formation in this sidewall model. There were reductions in the area of adhesion formation in the groups that received the higher doses of Pemirolast (Tables 3 and 4). The mean adhesion scores were: Placebo control: 100±0 (Table 1); 0.625 mg/ml Pemirolast: 90.0±4.9 (Table 2); 6.25 mg/ml Pemirolast: 77.1±7.1 ($p=0.007$; Table 3; 62.5 mg/ml Pemirolast: 71.4±6.7 ($p=0.001$; Table 4). There were also significant reductions in the tenacity of the adhesions formed in all groups of animals that received Pemirolast (by analysis of variance on the ranks).

At necropsy, there were no clinical signs associated with the administration of Pemirolast. However, there was inflammation observed at the abdominal cavity in 1 of 7 and 3 of 7 rabbits at the medium and high dose of drug, respectively. The results from this study are shown in Tables 1-4.

TABLE 1

Adhesion Scores in Placebo Treated Animals

| Animal Number | Adhesion Area Percentage | Adhesion Tenacity |
|---|---|---|
| 1 | 100 | 3 |
| 2 | 100 | 3 |
| 3 | 100 | 3 |
| 4 | 100 | 2 |
| 5 | 100 | 3 |
| 6 | 100 | 2 |
| 7 | 100 | 3 |

TABLE 2

Adhesion Scores in Animals Treated with
0.625 mg/ml Pemirolast

| Animal Number | Adhesion Area Percentage | Adhesion Tenacity |
|---|---|---|
| 1 | 100 | 2 |
| 2 | 70 | 1 |
| 3 | 100 | 2 |
| 4 | 100 | 1 |
| 5 | 80 | 1 |
| 6 | 100 | 1 |
| 7 | 80 | 1 |

TABLE 3

Adhesion Scores in Animals Treated with
6.25 mg/ml Pemirolast

| Animal Number | Adhesion Area Percentage | Adhesion Tenacity |
|---|---|---|
| 1 | 100 | 1 |
| 2 | 70 | 1 |
| 3 | 80 | 1 |
| 4 | 60 | 1 |
| 5 | 50 | 1 |
| 6 | 80 | 1 |
| 7 | 100 | 2 |

TABLE 4

Adhesion Scores in Animals Treated with
62.5 mg/ml Pemirolast

| Animal Number | Adhesion Area Percentage | Adhesion Tenacity |
|---|---|---|
| 1 | 100 | 1 |
| 2 | 50 | 1 |
| 3 | 70 | 2 |
| 4 | 80 | 1 |
| 5 | 70 | 2 |
| 6 | 50 | 1 |
| 7 | 80 | 2 |

Example 2

Spinal Model Evaluation of Pemirolast

Additional studies to confirm the efficacy of Pemirolast in the reduction of adhesion formation after spinal surgery are performed using a rabbit spinal laminectomy adhesion model.

In the rabbit spinal laminectomy model, a 2-level laminotectomy is performed at levels L5 and L3. Each rabbit is sedated using inhalation anesthesia (Isoflurane at 5.0%) via face mask. The lumbosacral area is then shaved and prepped with Betadine Scrub and 70 percent isopropyl alcohol solution. The rabbit is then placed in a prone position on the surgical table with slight lumbar flexion produced by a water bag placed beneath the abdomen. The lumbosacral area is covered with betadine solution and draped in an aseptic manner. A midline incision is made from level L6 up to level L2. The skin is separated from the underlying lumbodorsal fascia. An incision is done on the fascia exposing the subcutaneous tissues. After incising through the subcutaneous tissues, the muscles are subperiosteally dissected from the vertebral processes to expose the lamina and the ligamentum flavum. The muscles are retracted with the self-retaining retractor. Superficial bleeding is controlled by pressure. At the designated sites, a total laminectomy is performed by removal of the spinous process with careful excision of the laminae to the base of the mammillary process bilaterally. The ligamentum flavum and epidural fat are also removed in all animals, leaving clean dura exposed for the full extent of each laminectomy. Once the laminectomy site is prepared, bone bleeding is controlled with pressure and through the use of bone wax. The laminectomy defect is made to be approximately 5×10-mm in size. The dorsal surface of the dura is lightly abraded with a "ball" of 10 cm×10 cm sterile gauze (clamped in a pair of hemostats) for a period of 2 minutes to create abrasion trauma on the site of the bone defect. The test materials are then placed in the defect. The control animals received surgery only. The wound is then closed in layers without further irrigation. A single 3-0 silk suture was placed into the muscle directly above the laminectomy site to serve as a marker. Interrupted 0 Vicryl® sutures are used to approximate the lumbosacral fascia, followed by a continuous locking stitch of 4-0 Vicryl for the final fascia closure. The subcutaneous tissue is closed with interrupted 4-0 Vicryl® sutures. Interrupted 4-0 Prolene® sutures or skin staples are used to close the skin.

28 days post-surgery, the rabbits are euthanized with Eutha-6. The defect is examined based on the appearance of the surrounding tissues, the amount of blood on the surgical site and the amount of bone that regenerated on the surgical site. The vertebra are cut from each end of the defect and placed in a solution for 2 weeks after which decalcification is done and tissues are sent for histological evaluation.

The prepared slides are then evaluated microscopically for the presence of fibrosis, the density of the fibrosis, the vascularity at the fibrosis site and the presence or absence of the foreign body response. The area of the fibrosis is evaluated at 40× magnification by estimating the number of fields at that magnification that contained fibrotic material at the site of injury. The density of the fibrosis and the level of the foreign body reaction are evaluated and given a numerical score.

Example 3

A rotating disk (spinning disc) process is utilized to form poly(lactide) microspheres encapsulating Pemirolast. Poly (D,L-lactide), or PDLLA, is first dissolved in methylene chloride. Milled Pemirolast (5-10 µm) is then added to the polymer solution to make a suspension. The suspension is then placed on a rapidly rotating disc and through centrifugal force droplets (microspheres) of poly(lactide)-encapsulated Pemirolast are formed (congealed) and collected (on a cone). Several runs are conducted. Pemirolast/polymer ratios, disk parameters and polymer properties are described below. Microspheres ranged in size from 5 to 400 µm.

| PROCESS CONDITIONS FOR PEMIROLAST/PDLLA MICROSPHERE PREPARATION | | | | | |
|---|---|---|---|---|---|
| RUN | #1 | #2 | #3 | #4 | #5 |
| Pemirolast (gms) | 3.75 | 3.75 | 6.0 | 3.75 | 6.0 |
| Low IV-50/50 PDLLA 5% solvent solution (gms) | 225 | — | — | — | — |
| High IV-50/50 PDLLA 6% solvent solution (gms) | — | 187.5 | — | — | — |
| High IV-50/50 PDLLA 5% solvent solution (gms) | — | — | 180.0 | — | — |

-continued

PROCESS CONDITIONS FOR PEMIROLAST/PDLLA MICROSPHERE PREPARATION

| RUN | #1 | #2 | #3 | #4 | #5 |
|---|---|---|---|---|---|
| High IV-75/25 PDLLA 4% solvent solution (gms) | — | — | — | 281.25 | — |
| High IV-75/25 PDLLA 4% solvent solution (gms) | — | — | — | — | 225 |
| Disk Speed (RPM) | 4 K | 4 K | 4 K | 4 K | 4 K |
| Disk Temp (° C.) | RT | RT | RT | RT | RT |
| Disk Size (Inch) | 3 | 3 | 3 | 3 | 3 |
| Inside Cone Air Temp (° C.) | 50 | 50 | 50 | 50 | 50 |
| Pemirolast/Polymer solution Flow Rate (gms/Min) | 90 | 90 | 90 | 90 | 90 |

Drug/polymer ratios (wt/wt) of 25/75 is used in run #1, #2, and #3 and 40/60 in run #4 and #5.

Once prepared, the microspheres are mixed with an aqueous gel to form an injectable adhesion prevention material useful for post-operative adhesion, for example, in the spine. This material is used to form a physical barrier comprising the aqueous gel having the Pemirolast sustained release microspheres incorporated therein.

For example, a 3% (wt/vol) aqueous buffered gel of a sodium salt of carboxymethyl cellulose is prepared by mixing under high shear 3 grams of a 300 kDa dry sodium carboxymethyl cellulose powder into 100 ml of buffered saline in a glass vial. After 10 minutes of mixing, a homogenous gel is obtained. The gel is then autoclaved using standard techniques to yield a sterilized sodium carboxymethyl cellulose. Microspheres (1 gram) from run #1 are also sterilized using standard gamma irradiation techniques. The 1 gram of microspheres is then mixed into the gel under aseptic conditions to form a sterile injectable-adhesion prevention material. Seven 0.5 mls of injectable sodium carboxymethyl cellulose gel and PDLLGA microspheres of encapsulated Pemirolast are then transferred to seven 1 ml syringes under aseptic conditions and packaged for preparation for sterile surgery. Each of the contents of the seven syringes is then implanted in seven rabbits in the laminectomy model as described in Example 2 in order to demonstrate the materials efficacy.

While the fundamental novel features of the invention have been shown and described, it will be understood that various omissions, substitutions and changes in the form and details illustrated may be made by those skilled in the art without departing from the spirit of the invention. It is the intention, therefore, to be limited only as indicated by the scope of the following claims.

We claim:

1. A delivery vehicle suitable for local, non-systemic administration of a drug to a body and directly to tissue within a body cavity having been subjected to a surgical procedure, said vehicle comprising Pemirolast or an analog thereof in an amount effective to inhibit formation of post-operative adhesions upon local, non-systemic administration of said Pemirolast to said tissue, wherein the delivery vehicle is selected from the group consisting of microcapsules, microspheres, barriers, liposomes, fibers, filaments, gels, foams and films, and wherein said delivery vehicle comprises a polymer selected from the group consisting of poloxamers, poly(orthoester)s, poly(vinyl alcohol)s, poly(anhydride)s, poly(methacrylate)s, poly(methacryladmide)s, anionic carbohydrate polymers, poly(hydroxybutyric acid)s, polyacetals, poly(l-lactide), poly(dl-lactide), poly(dl-lactide-co-glycolide)s, poly(l-lactide-co-glycolide)s, poly(e-caprolactone), polyglycolide, poly(p-dioxanone)s, poly(trimethylene carbonate), poly(alkylene diglycolate)s, poly(oxaester)s, poly(oxaamide)s and glyceride polymers, and the Pemirolast or analog thereof is present in an amount of from about 0.01 milligram Pemirolast or analog thereof per kilogram of the body to about 3,000 milligram Pemirolast or analog thereof per kilogram of the body.

2. The delivery vehicle of claim 1 wherein said liposome is selected from the group consisting of L-alpha-distearoyl phosphatidylcholine, phosphatidylcholine, dipalmitoylphosphatidylcholine and egg phosphatidylcholine.

3. The delivery vehicle of claim 1 wherein said vehicle comprises a crystalloid instillate selected from the group consisting of phosphate buffered saline, saline and lactated Ringer's solution.

4. The delivery vehicle of claim 1 wherein said vehicle comprises viscous instillate comprising a carrier selected from the group consisting of dextrans, cyclodextrans, hydrogels, carboxymethylcellulose, poly(saccharide)s, hyaluronic acids, crosslinked hyaluronic acids and chondroitin sulfates.

5. The delivery vehicle of claim 4 wherein said barrier is selected from the group consisting of hyaluronic acids, cellulosics derivatives, collagens, recombinant human collagen, polyethylene glycols, pluronics, chitin, chitosans, dextrans, glucoses, carbohydrates, gelatins, glycosaminoglycans, polyacrylamides, polyvinyl pyrrolidones, polyvinyl alcohols, polymethyacrylics, aliginates, starches and polypeptides.

6. The delivery vehicle of claim 1 additionally comprising a second therapeutic agent in an amount effective to provide the therapeutic effect intended by administration of said therapeutic agent.

7. The delivery vehicle of claim 6 wherein said therapeutic agent is selected from the group consisting of an anti-platelet, an anti-fibrotic, an anti-inflammatory, an anti-proliferative and an agent that inhibits collagen synthesis.

8. The delivery vehicle of claim 1 wherein said vehicle provides for single dose administration of said Pemirolast or analog thereof.

9. A composition suitable for local, non-systemic administration of a drug to a body and directly to tissue within a body cavity having been subjected to a surgical procedure, said composition comprising Pemirolast or an analog thereof in an amount effective to inhibit formation of post-operative adhesions upon local, non-systemic administration of said composition to said tissue, and a carrier suitable for local, non-systemic administration of said Pemirolast or analog thereof, wherein the delivery vehicle is selected from the group consisting of microcapsules, microspheres, barriers, liposomes, fibers, filaments, gels, foams and films, and wherein said delivery vehicle comprises a polymer selected from the group consisting of poloxamers, poly(orthoester)s, poly(vinyl alcohol)s, poly(anhydride)s, poly(methacrylate)s, poly(methacryladmide)s, anionic carbohydrate polymers, poly(hydroxybutyric acid)s, polyacetals, poly(l-lactide), poly(dl-lactide), poly(dl-lactide-co-glycolide)s, poly(l-lactide-co-glycolide)s, poly(e-caprolactone), polyglycolide, poly(p-dioxanone)s, poly(trimethylene carbonate), poly(alkylene diglycolate)s, poly(oxaester)s, poly(oxaamide)s and glyceride polymers, and the Pemirolast or analog thereof is present in an amount of from about 0.01 milligram Pemirolast or analog thereof per kilogram of the body to about 3,000 milligram Pemirolast or analog thereof per kilogram of the body.

10. The composition of claim 9 wherein said composition provides for single dose administration of said Pemirolast or analog thereof.

11. The composition of claim 9 wherein said liposome is selected from the group consisting of L-alpha-distearoyl phosphatidylcholine, phosphatidylcholine, dipalmitoylphosphatidylcholine and egg phosphatidylcholine.

12. The composition of claim 9 wherein said vehicle comprises a crystalloid instillate selected from the group consisting of phosphate buffered saline, saline and lactated Ringer's solution.

13. The composition of claim 9 wherein said vehicle comprises viscous instillate comprising a carrier selected from the group consisting of dextrans, cyclodextrans, hydrogels, carboxymethylcellulose, poly(saccharide)s, hyaluronic acids, crosslinked hyaluronic acids and chondroitin sulfates.

14. The composition of claim 9 wherein said barrier is selected from the group consisting of hyaluronic acids, cellulosics derivatives, collagens, recombinant human collagen; polyethylene glycols, pluronics, chitin, chitosans, dextrans, glucoses, carbohydrates, gelatins, glycosaminoglycans, polyacrylamides, polyvinyl pyrrolidones, polyvinyl alcohols, polymethyacrylics, aliginates, starches and polypeptides.

15. The composition of claim 9 additionally comprising a second therapeutic agent in an amount effective to provide the therapeutic effect intended by administration of said therapeutic agent.

16. The composition of claim 15 wherein said therapeutic agent is selected from the group consisting of an anti-platelet, an anti-fibrotic, an anti-inflammatory, an anti-proliferative and an agent that inhibits collagen synthesis.

\* \* \* \* \*